United States Patent [19]

Sak

[11] Patent Number: 5,562,103

[45] Date of Patent: Oct. 8, 1996

[54] PHLEBOTOMY SYSTEM HAVING RETRACTABLE NEEDLE CANNULA

[76] Inventor: Robert F. Sak, 9674 Colorado Ct., Boca Raton, Fla. 33434

[21] Appl. No.: 417,049

[22] Filed: Apr. 4, 1995

[51] Int. Cl.⁶ .................................................. A61B 5/00
[52] U.S. Cl. ................................. 128/763; 604/194
[58] Field of Search ...................... 604/110, 195, 604/196, 208, 209, 210, 225, 187, 263; 128/763, 764, 765

[56] References Cited

U.S. PATENT DOCUMENTS

| | | |
|---|---|---|
| 3,656,472 | 4/1972 | Ben Moura . |
| 4,026,287 | 5/1977 | Haller . |
| 4,398,544 | 8/1983 | Nugent et al. . |
| 4,592,744 | 6/1986 | Jagger et al. . |
| 4,643,199 | 2/1987 | Jennings, Jr. et al. . |
| 4,804,370 | 2/1989 | Haber et al. . |
| 4,808,169 | 2/1989 | Haber et al. . |
| 4,813,936 | 3/1989 | Schroeder . |
| 4,838,870 | 6/1989 | Haber et al. . |
| 4,850,374 | 7/1989 | Diaz-Ramos . |
| 4,931,040 | 6/1990 | Haber et al. ............................ 604/110 |
| 4,950,241 | 8/1990 | Ranford . |
| 4,995,870 | 2/1991 | Baskas . |
| 5,047,016 | 9/1991 | Dolgin et al. . |
| 5,086,780 | 2/1992 | Schmitt ................................... 128/763 |
| 5,188,597 | 2/1993 | Sweeney et al. . |
| 5,201,716 | 4/1993 | Richard ................................... 604/187 |
| 5,221,262 | 6/1993 | Kite . |
| 5,382,235 | 1/1995 | Sak . |

*Primary Examiner*—Max Hindenburg
*Assistant Examiner*—Pamela L. Wingood
*Attorney, Agent, or Firm*—Banner & Allegretti, Ltd.

[57] ABSTRACT

A phlebotomy system including a needle assembly, a retraction assembly, and a cylindrical barrel. The needle assembly includes a needle cannula with first and second ends, a needle sleeve for supporting the needle cannula and having a flared proximal end, and a hub into which the needle sleeve is inserted. The cylindrical barrel is threadedly secured to the hub. The retraction assembly includes a central plate with a central opening through which the needle sleeve extends. When a downward force is applied to the retraction assembly, the retraction assembly to moved to an active position such that a locking port is axially aligned with and thereby engages the needle sleeve. Hence, the locking port engages the flared proximal end of the needle sleeve when the retraction assembly is moved rearward and the needle cannula is retracted into the barrel. In an alternative embodiment, the needle sleeve is threadedly engaged with the central opening of the retraction assembly and rearward movement of the retraction assembly likewise results in retraction of the needle cannula into the barrel.

20 Claims, 10 Drawing Sheets

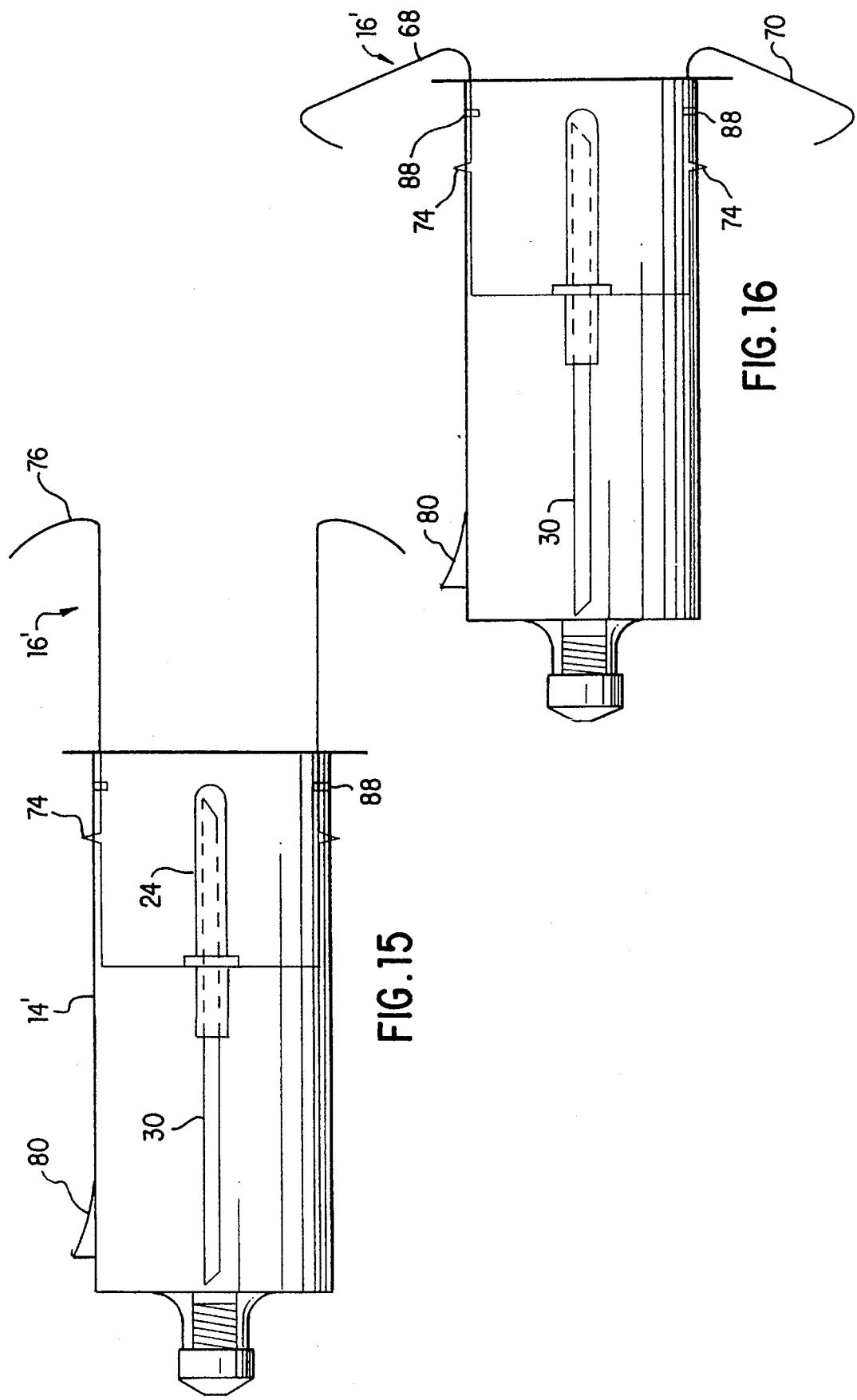

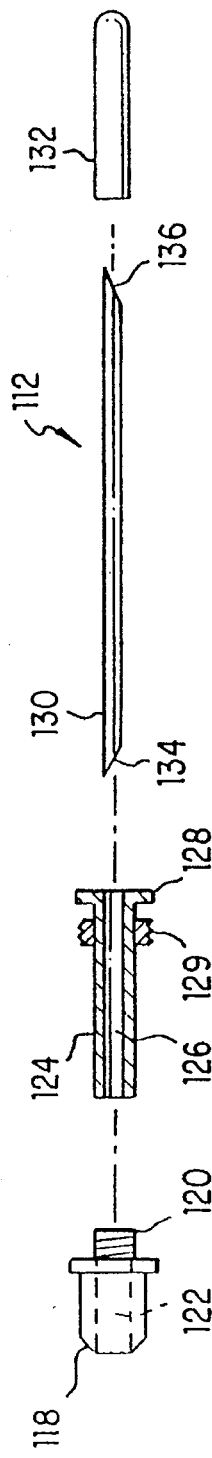
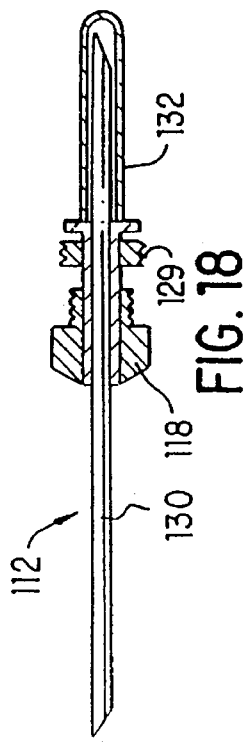
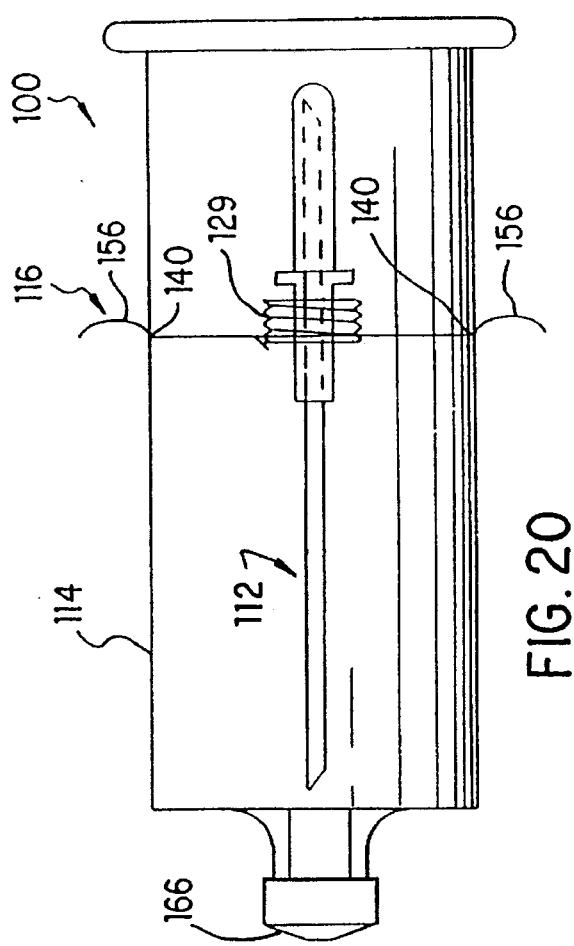

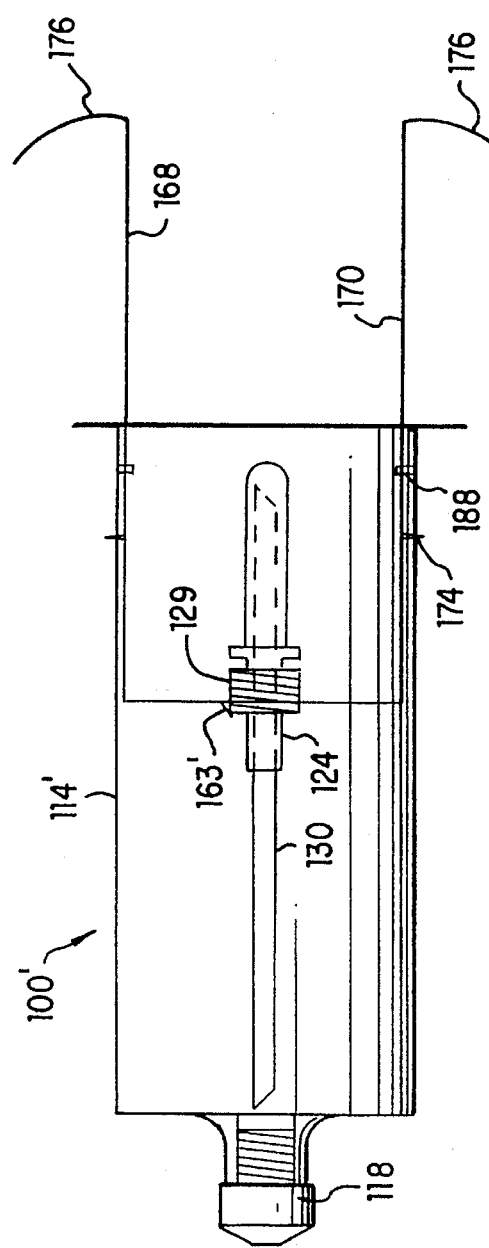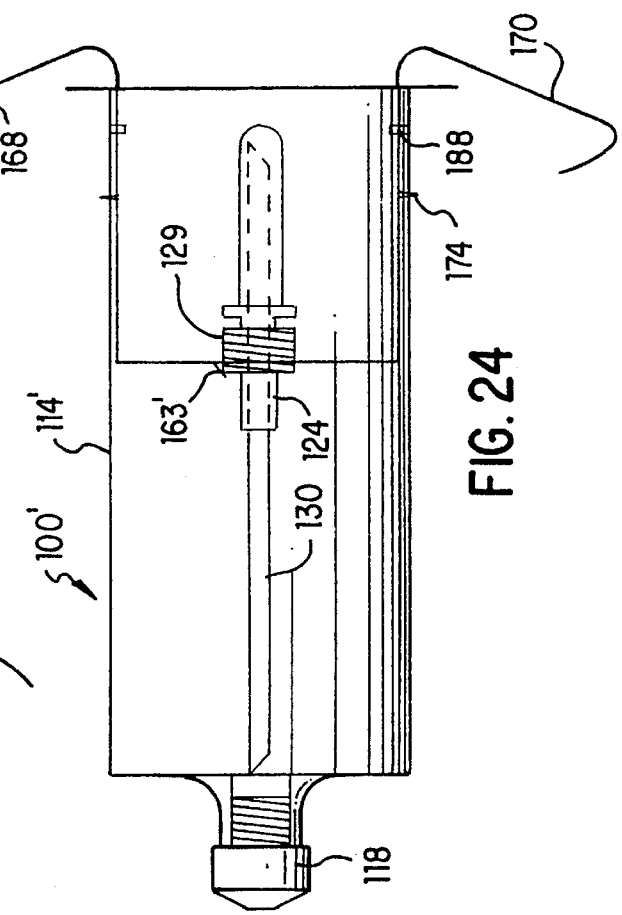

PHLEBOTOMY SYSTEM HAVING RETRACTABLE NEEDLE CANNULA

TECHNICAL FIELD

This invention relates to a vacuum tube phlebotomy system for the withdraw of blood and, more particularly, to a system with a retractable needle that is designed to protect an operator from being inadvertently infected or injured by the used needle thereof.

BACKGROUND OF THE INVENTION

Referring to FIG. 1, a typical prior art phlebotomy system or blood sampler "bs" used for the withdraw of blood generally has a double ended hollow needle or needle cannula "n", a cylindrical barrel or holder for the needle "b", and a vacuum tube or evacuated receptacle "r". A first end "fe" of the double ended needle is inserted into a vein and the second end "se" is adapted to be inserted through a puncturable cover "c" of the evacuated receptacle. The second end of the needle has a rubber sleeve "s" thereover which operates as a valve and is pushed down over the second end of the needle as the puncturable cover of the evacuated container is pushed onto the needle. As soon as the second end of the needle emerges on the other side of the cover inside the receptacle, the vacuum therein instantly draws a sample of blood into the receptacle. An advantage of this arrangement is that with the first end of the needle still inserted into the vein, an operator, such as a nurse or lab technician, can collect a number of samples for different types of blood tests by merely inserting in succession a number of vacuum tubes over the second end of the needle. The described phlebotomy system is well-known in the art under the brand name Becton Dickinson VACUTAINER Systems, located in Rutherford, N.J.

A problem with the vacuum tube phlebotomy system as just described is that when the first end of the needle is withdrawn from the vein, it remains exposed and can be a source of great danger to the operator or to anyone who might be pricked or scratched by the exposed end of the needle. Needle injuries may result in the transmission of diseases such as hepatitis and HIV and may also lead to infection. One common solution available to the operator was to simply drop the needle and its holder into a trash receptacle. Another solution is to attempt to recap the needle with a safety cover immediately after use. This, however, may in itself cause injury if the operator should accidently stick themselves during the recapping process.

SUMMARY OF THE INVENTION

The present invention lessens the danger of being injured or infected by a used needle cannula by providing a needle cannula that is secured in its extended position for the blood withdrawal process and then retracted into the barrel upon completion of the blood withdrawal process.

The phlebotomy system of the present invention provides a needle assembly, a retraction assembly, and a cylindrical barrel. The needle assembly includes a needle cannula having first and second ends, a needle sleeve with a flared proximal end for supporting the needle cannula, and a hub into which the needle sleeve is inserted. The retraction assembly includes a central plate with a central opening through which the needle sleeve extends. The cylindrical barrel is threadedly secured to the hub such that the first end of the needle cannula extends therefrom when the retraction assembly is disposed in a passive position. The needle cannula may be moved to a retracted position within the cylindrical barrel when the retraction assembly is moved to an active position.

The central opening through the central plate includes a larger access port and a tapered locking port. When the needle cannula is positioned in its normal extended position, the access port is aligned with the needle sleeve which passes through a distal end of the cylindrical barrel. When a downward force is applied to the retraction assembly, the retraction assembly is repositioned to the active position such that the locking port is axially aligned with the distal end of the barrel and thereby engages the needle sleeve. Upon rearward movement of the retraction assembly in the active position, the locking port engages the flared proximal end of the needle sleeve and retracts the needle sleeve, including the needle cannula, into the interior of the cylindrical barrel.

Alternatively, the central opening through the central plate includes a single opening and the needle sleeve includes a threaded portion. The needle sleeve may thereby be threadedly secured to the central plate. Accordingly, upon rearward movement of the retraction assembly, the needle sleeve holding the needle cannula is retracted into the interior of the cylindrical barrel.

In a first preferred embodiment of the present invention, the cylindrical barrel has a plurality of slide openings along the axial length of the barrel and the retraction assembly includes an upper extension extending through a first of the slide openings and a lower extension extending through a second of the slide openings. Thus, the retraction assembly is moved axially along the slide openings toward a proximal end of the barrel in order to retract the needle cannula into the barrel.

In a second preferred embodiment of the present invention, the retraction assembly is positioned within the barrel. The retraction assembly has a generally U-shaped configuration including an upper leg, a lower leg, and a base portion extending therebetween. The upper leg extends adjacent an interior upper surface of the barrel and the lower leg extends adjacent an interior opposing lower surface of the barrel. The upper and lower legs extend past the proximal end of the barrel to define a pull mechanism for moving the retraction assembly. Thus, a force is applied to the pull mechanism to move the retraction assembly axially along the interior of the barrel toward the proximal end thereof and thereby retract the needle cannula into the barrel.

BRIEF DESCRIPTION OF THE DRAWINGS

The above description and other objects, advantages and features of the present invention will be more fully understood and appreciated by reference to the specification and accompanying drawings, wherein:

FIG. 15 is a side view of the phlebotomy system in accordance with the second embodiment of the present invention with the needle in a retracted position within the barrel;

FIG. 16 is a side view of the phlebotomy system in accordance with the second embodiment of the present invention with the retraction assembly in an alternative retracted position;

FIG. 17 is an exploded view of a needle assembly used in a phlebotomy system in accordance with a third embodiment of the present invention;

FIG. 18 is an assembled view of the needle assembly shown in FIG. 17;

FIG. 20 is a side view of the phlebotomy system in accordance with the third embodiment of the present invention with the needle in a retracted position;

FIG. 23 is a side view of the phlebotomy system in accordance with the fourth embodiment of the present invention with the needle in a retracted position within the barrel; and FIG. 24 is a side view of the phlebotomy system in accordance with the fourth embodiment of the present invention with the retraction assembly in an alternative retracted position.

DETAILED DESCRIPTION OF THE PREFERRED EMBODIMENTS

Figure 1:
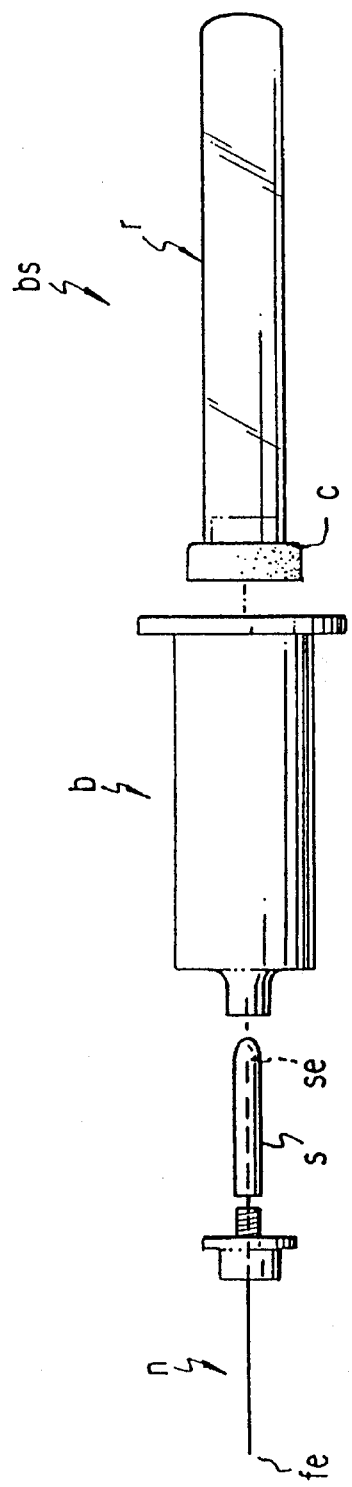
FIG. 1 is an exploded view of a prior art vacuum tube phlebotomy system.
Figure 2:
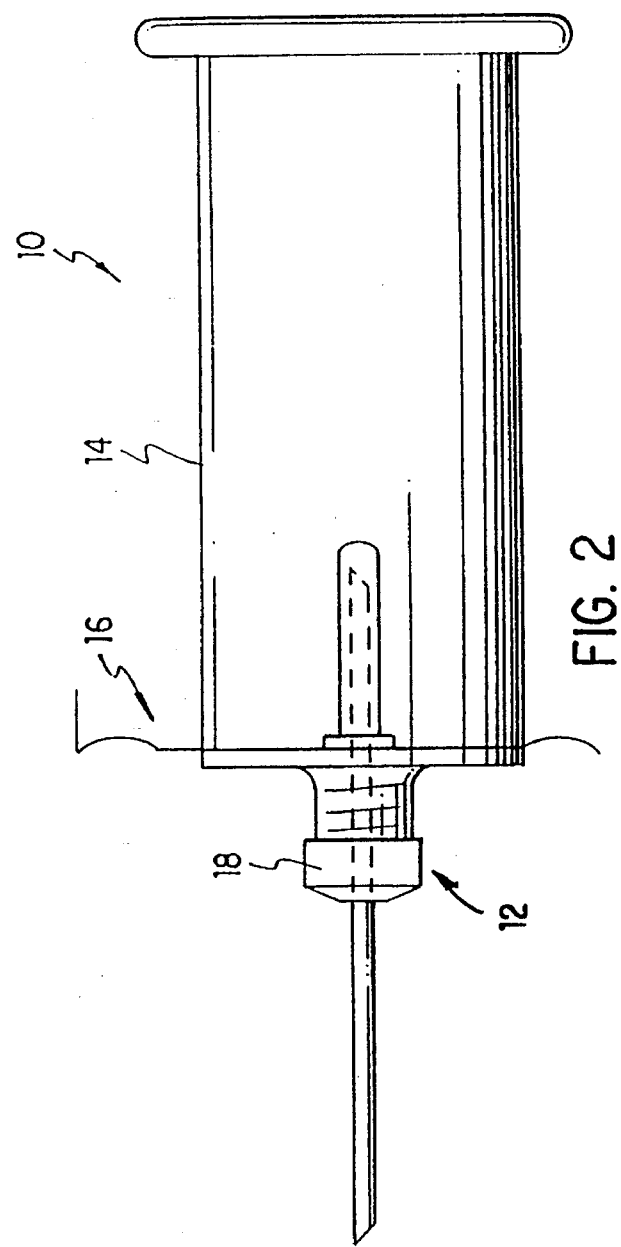
FIG. 2 is a side view of a phlebotomy system in accordance with a first embodiment of the present invention with the needle in an extended position.

Referring to FIG. 2, a phlebotomy system or blood sampler 10 is generally shown in accordance with the present invention. Sampler 10 includes a needle assembly 12, a canister or barrel 14, and a retraction assembly 16, each of which is discussed in detail below. Phlebotomy system 10 allows for the retraction of the needle cannula into the barrel after completion of the blood withdrawal process and thus reduces the risk of injury, infection or disease to the technician. Although not illustrated, it should be clear to one skilled in the art that an evacuated receptacle or vacuum tube such as that shown in FIG. 1 is attached to needle assembly 12 in the same manner as it is attached to double ended needle "n" of the prior art. For like components, phlebotomy system 10 is preferably constructed with the same materials currently in use in the prior art systems.

Figure 3:
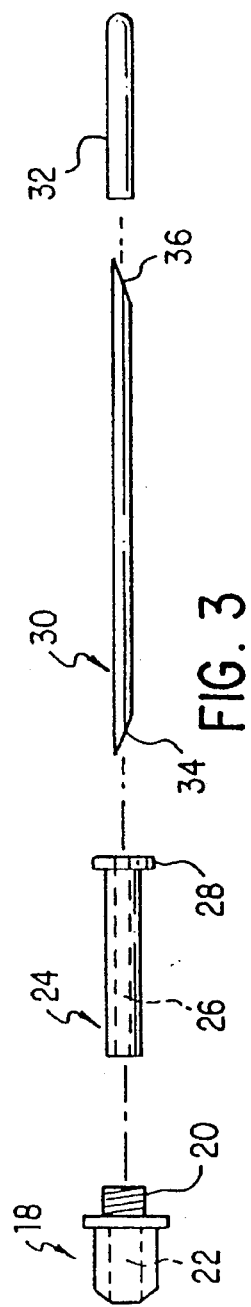
FIG. 3 is an exploded view of a needle assembly used in the phlebotomy system of FIG. 2.
Figure 4:
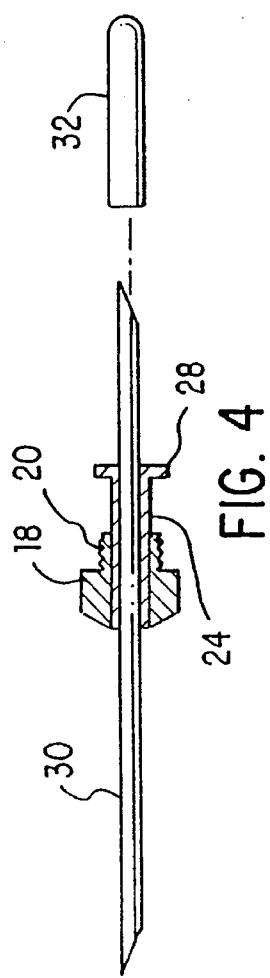
FIG. 4 is an assembled view of the needle assembly shown in FIG. 3.

In a preferred embodiment of the present invention, needle assembly 12 includes a hub 18 having a hollow core 22 extending axially therethrough and a threaded proximal end 20, a needle sleeve 24 having a hollow core 26 extending axially therethrough and a flared proximal end 28, a double ended needle or needle cannula 30, and a rubber sleeve or flow inhibitor 32, as shown in FIGS. 3 and 4. The hollow core 22 of hub 18 has an inner diameter approximately equal to the outer diameter of needle sleeve 24 such that the sleeve 24 may be inserted into the hollow core 22 of hub 18 in the assembled state. Similarly, the hollow core 26 of needle sleeve 24 has an inner diameter approximately equal to the outer diameter of needle cannula 30 such that needle cannula 30 may be securely positioned in the sleeve 24 within hub 18. As illustrated, a first end 34 of needle cannula 30 extends through the distal end of the sleeve and hub for insertion into a vein and the second end extends through the flared proximal end 28 for attachment to an evacuated receptacle. The rubber flow inhibitor 32 is installed over the second end 36 of needle 30 and then stretched to fit over the flared proximal end 28 of the needle sleeve 24. In addition, a protective cover (not shown) may be installed over the first end 34 of the needle until such time as when an operator or technician is ready to draw blood.

Figure 5:
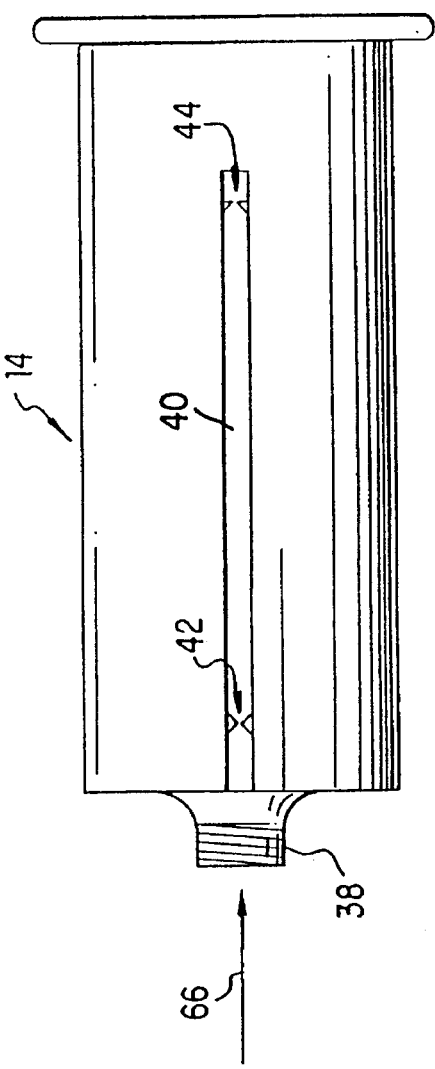
FIG. 5 is a top view of a barrel used in the phlebotomy system of FIG. 2.

Referring to FIG. 5, a cylindrical canister or barrel 14 in accordance with a first embodiment of the present invention includes a threaded distal end 38 for obtaining a threaded attachment to the threaded end 20 of hub 18. Barrel 14 further includes opposing slide openings 40 extending approximately three quarters axially the length of the barrel. In a preferred embodiment, two rectangular shaped slide openings 40 extend along the length of barrel 14 far enough to allow the full retraction of the needle within the barrel and are therefore dependent upon the size of the phlebotomy system. Slide openings 40 each preferably include a forward slide stop 42 and a rear slide stop 44, the purpose of which will be described further below.

Figure 7:
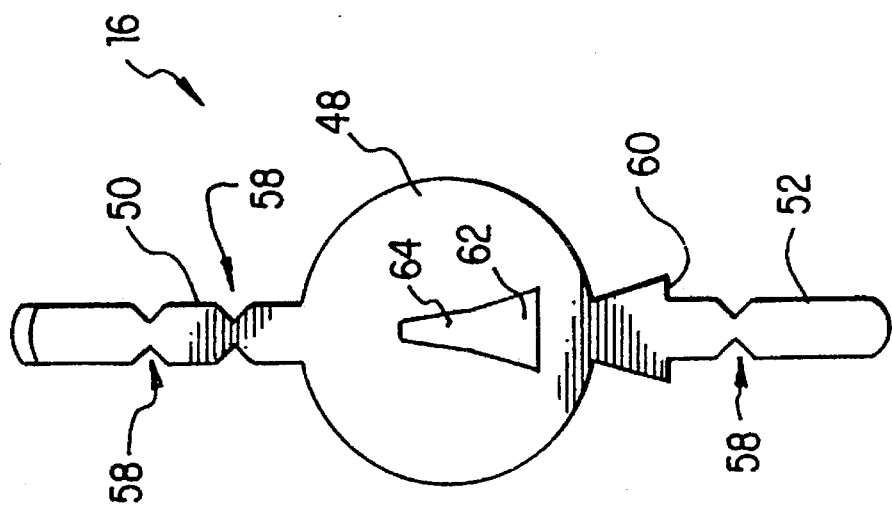
FIG. 7 is a front view of the retraction assembly shown in FIG. 6.
Figure 6:
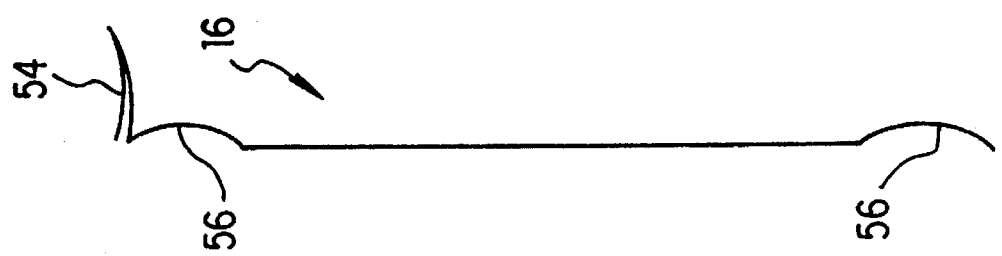
FIG. 6 is a side view of a retraction assembly used in the phlebotomy system of FIG. 2.
Figure 8:
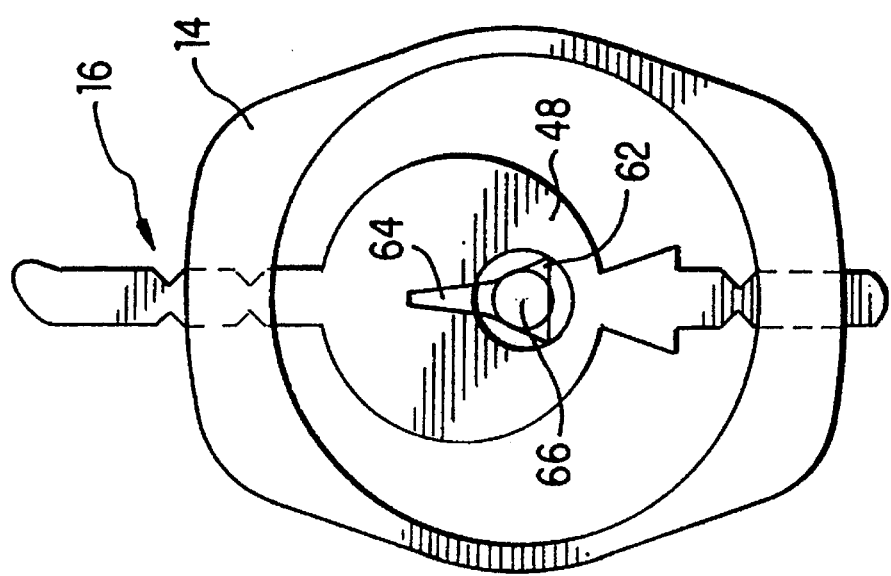
FIG. 8 is a front view of the retraction assembly disposed within the barrel in a passive state.
Figure 14:
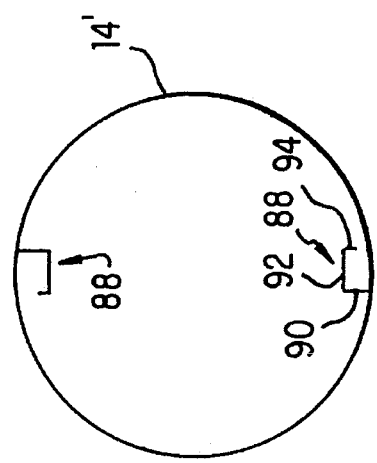
FIG. 14 is an end view of a barrel used in the phlebotomy system shown in FIG. 11.

Retraction assembly 16 in accordance with a first embodiment of the present invention is shown in FIGS. 6 and 7 and is illustrated positioned within barrel 14 in FIGS. 2 and 8. Retraction assembly 16 includes a central plate 48, an upper extension 50 extending upward therefrom and a lower extension 52 extending downward therefrom. The upper extension 50 has a thumb tab 54 and finger grip 56 and lower extension 52 also has a finger grip 56 in order to assist the operator or technician in the proper use and positioning of the present invention. A plurality of position indents 58 are disposed on upper and lower extensions 50, 52 in order to axially position the retraction assembly 16 within barrel 14. Position indents 58 correspond in shape to the forward slide stops 42 located within slide openings 40. Thus, axial movement of retraction assembly 16 past forward slide stops 42 is prevented in the position of FIG. 8. When a downward force is applied to retraction assembly 16, the downward movement creates alignment of position indents 58 on the upper and lower extensions 50, 52 with the forward slide stops 42. Thereafter, retraction assembly 16 is free to move axially rearward along slide openings 40. A position stop 60 is also disposed on lower extension 52 in order to limit the downward movement of retraction assembly 16. As shown most clearly in FIG. 7, central plate 48 includes a central opening or access port 62 extending therethrough with the lower portion of access port 62 being greater in size than the upper portion of the access port 62. More specifically, the upper portion of access port tapers to define a locking port 64, the function of which is described below. Retraction assembly 16 is preferably constructed from a chemically non-reactive material such as, by way of example, 301 SST shim stock, full hard cold rolled 18/8 chrome nickel alloy, with Rockwell 40/45 at 0.025.

The above components of phlebotomy system 10 of the present invention are assembled for use in the following arrangement. The upper extension 50 of retraction assembly 16 extends through a first of the slide openings 40 and the lower extension 52 extends through a second of the slide openings 40. Retraction assembly 16 is positioned in a passive position within barrel 14 (shown in FIG. 2) in that retraction assembly 16 is positioned adjacent the forward slide stops 42 and access port 62 is aligned with the distal end opening 66 of barrel 14, as shown in FIG. 8. In addition, slide stops 42 prevent the rearward movement of the retraction assembly 16. Needle sleeve 24 containing needle cannula 30 and rubber flow inhibitor 32 passes through the distal end opening 66 and access port 62 such that the second end 36 of the needle cannula and the flared proximal end 38 of the needle sleeve 24 are positioned adjacent retraction assembly 16 within the barrel 14 on the proximal side of retraction assembly 16. The first end 34 of needle cannula 30 extends through the distal opening 66 of barrel for insertion into a vein and may be provided with a protection cover (not shown). The threaded distal end 38 of barrel 14 is connected by screw thread engagement with the threaded proximal end 20 of the hub 18. This in turn secures the needle assembly 12 and the retraction assembly 16 within barrel 14 and phlebotomy system 10 is ready for rise.

As in the prior art, the first end 34 of double ended needle cannula 30 is inserted into a vein. The second end 36 of the needle 30 has rubber sleeve or flow inhibitor 32 thereover which operates as a valve which is pushed down over the second end of the needle 30 as the puncturable cover of the evacuated container is pushed onto the needle. As soon as the second end 36 of the needle 30 emerges on the other side of the puncturable cover inside the vacuum tube or other evacuated receptacle, the vacuum therein instantly draws a sample of blood into the receptacle. Thus, the operator, nurse or lab technician, can collect the required number of samples for different types of blood tests by merely inserting in succession a number of tubes or receptacles over the second end 36 of the needle 30.

When the blood withdrawal process is complete, the operator using the blood sampler 10 of the present invention preferably removes the needle from the patient's vein and then retracts needle 30 into the cylindrical compartment of barrel 14, as described below, and thereby reduces the risk of injury or transmission of disease from a used needle. The needle could also conceivably be retracted into the barrel directly from the vein, however, this procedure may tend to cause uneasiness in most patients.

Figure 9:
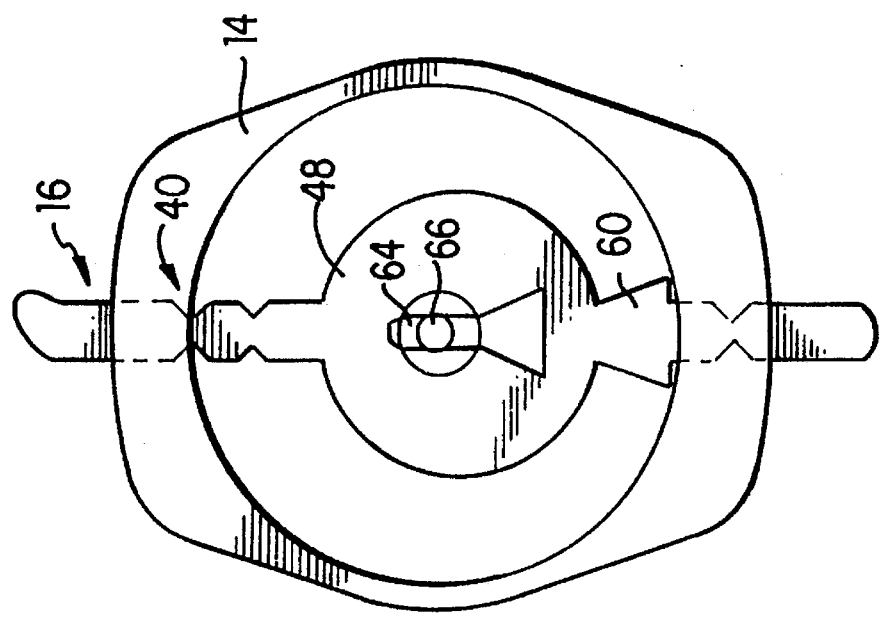
FIG. 9 is a front view of the retraction assembly disposed within the barrel in an active state.

More preferably, the operator applies a force to thumb tab 54 which in turn causes a downward movement of retraction assembly 16. The uppermost position indent 58 on the upper extension 50 aligns with one forward slide stop 42 and the position indent 58 on the lower extension 52 aligns with the opposing forward slide stop 42 such that retraction assembly is free to move axially rearward within the slide openings. As illustrated in FIG. 9, retraction assembly 16 is thereby positioned in the active state. Position stop 60 is adjacent the inner wall of the barrel 14 to limit the downward movement of retraction assembly 16 relative to the opposing slide opening. In addition, the distal opening 66 of barrel 14 is now aligned with locking port 64 such that the needle sleeve 24 passing through distal opening 66 is engaged by locking port 64 of the retraction assembly 16.

Figure 10:
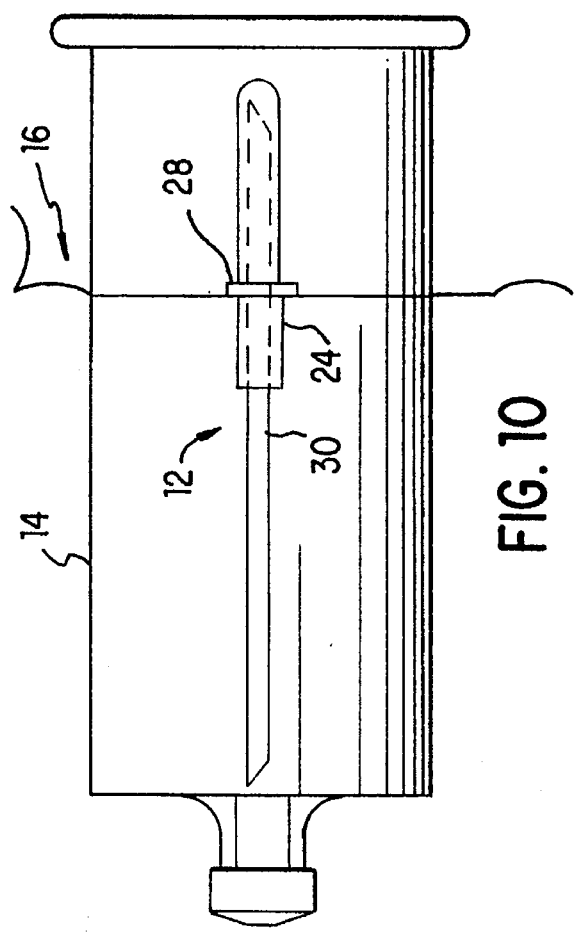
FIG. 10 is a side view of the phlebotomy system in accordance with the first embodiment of the present invention with the needle in a retracted position within the barrel.
Figure 13:
FIG. 13 is a side view of an engagement lever used in the phlebotomy system shown in FIG. 11.

Referring to FIG. 10, position indents 58 aligning with slide openings 40 allow retraction assembly 16 to move axially past forward slide stops 42. Further rearward movement of the retraction assembly 16 within slide openings 40 thereafter engages the flared proximal end 28 of the needle sleeve and causes a corresponding movement of the needle sleeve in the rearward direction. As the needle sleeve 24 is moved rearward, the needle cannula 30 is retracted rearward through the hub 18 and into the cylindrical interior of the barrel 14. Rear slide stops 44 terminate the movement of retraction assembly 16 and signal that the used needle cannula 30 is safely contained within barrel 14. The barrel and needle may then be safely disposed of without risk of injury. In addition, phlebotomy system 10 prevents the needle 30 from accidently being reused. That is, there is no mechanism for extending needle cannula 30 and needle sleeve 24 through hub 18. Therefore, the operator is assured that needle cannula 30 will not be reused.

Referring to FIGS. 11–15, retraction assembly 16' is configured for insertion into barrel 14' in accordance with a second embodiment of the present invention. Retraction assembly 16' has a narrow, generally U-shaped configuration generally corresponding to that of barrel 14'. Retraction assembly 16' has an upper leg 68, a lower leg 70, and a base portion 72 extending therebetween and joining together the opposing legs. Base portion 72 includes the central plate 48 having an access port 62 and locking port 64 identical to those described above for retraction assembly 16. Each leg 68, 70 includes a pull tab 76 for gripping retraction assembly 16' and moving it axially along the length of barrel 14' and a stop tab 74 which limits the axial movement of retraction assembly 16'.

Cylindrical canister or barrel 14' in accordance with the second embodiment of the present invention includes a threaded distal end 38' for obtaining a threaded attachment to the threaded end 20 of hub 18. Needle assembly 12 is identical to that described above for the first embodiment of the invention. Barrel 14' further includes a ridge 78 disposed around the interior periphery thereof, or alternatively, at least on opposing surfaces corresponding to the location of assembly 16'. In a preferred embodiment, ridge 78 is spaced far enough from the proximal end of barrel 14' in order to engage stop tabs 74 and thereby limit the axial movement of retraction assembly 16' when the needle is fully retracted within the barrel. Barrel 14' also includes guide arms 88 which are preferably integrally molded with barrel 14'. Each guide arm 88 has an inward segment 90 extending toward the interior of barrel 14', a transverse segment 92, and a retaining segment 94 which defines an open space between the interior wall of barrel 14' for the insertion of retraction assembly 16'. Guide arms 88 are utilized to maintain the position of retraction assembly 16' flush with the interior cylindrical surface of barrel 14' and the proper alignment of stop tabs 74 with ridge 78. Thus, retraction assembly 16' is inserted into barrel 14' and rotated in a clockwise direction at the point of manufacture, in the preferred embodiment, in order to lock the upper and lower legs 68,70 into position within guide arms 88.

Figure 11:
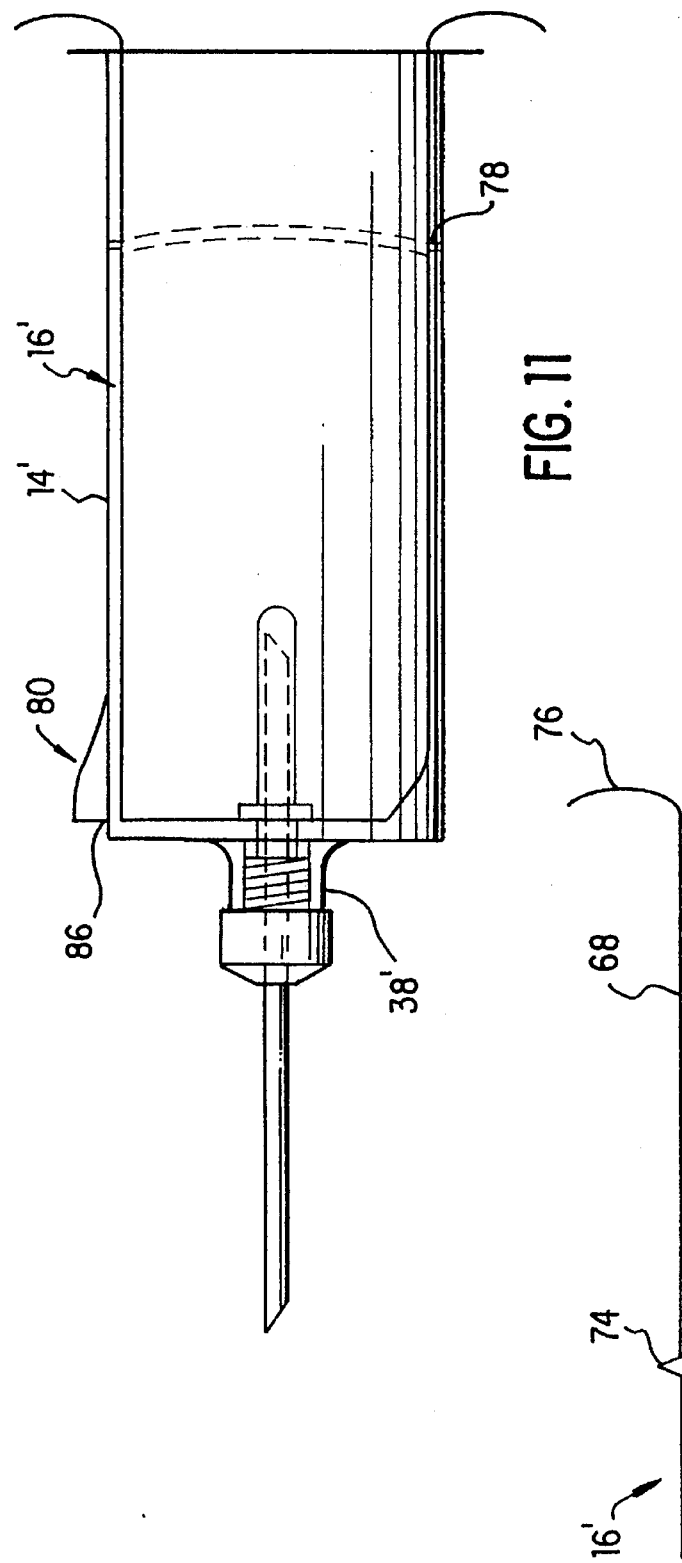
FIG. 11 is a side view of a phlebotomy system in accordance with the second embodiment of the present invention with the needle in an extended position.
Figure 12:
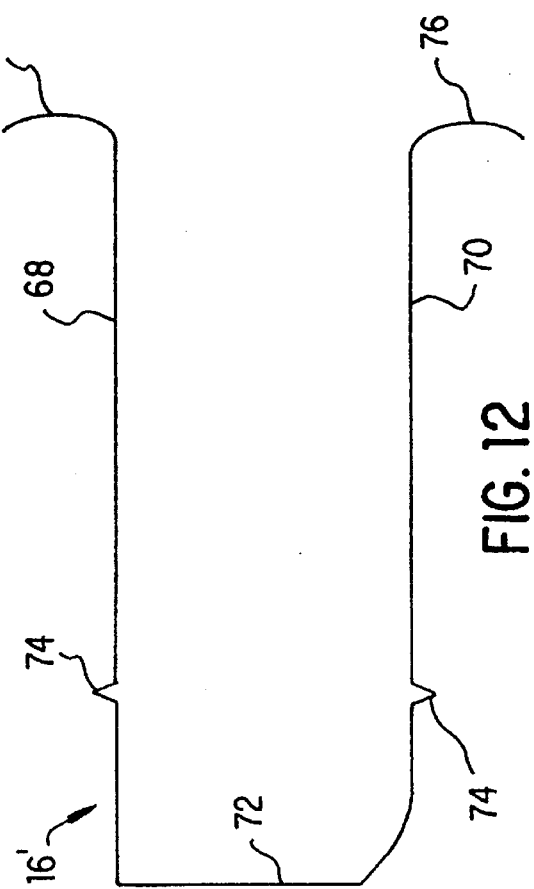
FIG. 12 is a side view of a retraction assembly used in the phlebotomy system shown in FIG. 11.
Figure 21:
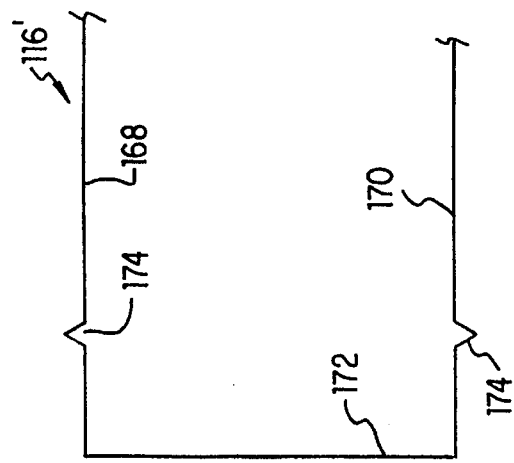
FIG. 21 is a side view of a retraction assembly of the phlebotomy system in accordance with a fourth embodiment of the present invention.
Figure 22:
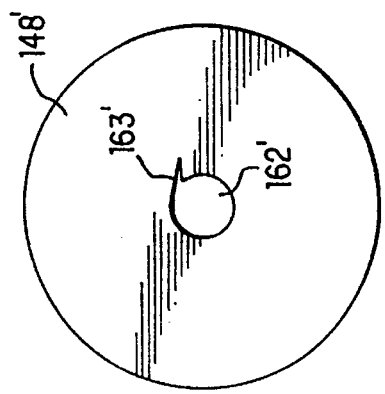
FIG. 22 is a front view of the central plate of the retraction assembly of the phlebotomy system in accordance with a fourth embodiment of the present invention.

Mounted on top of barrel 14' is an engagement lever 80 which is normally biased in a first position when retraction assembly 16' is in the passive position as shown in FIG. 11. An opening 86 is provided in barrel 14' sized for the insertion of the vertical portion 84 of engagement lever 80. More specifically, when a force is applied to the axial portion 82 of engagement lever 80, the downward movement thereof causes the vertical portion 84 to pass through opening 86 in barrel 14' and contact the upper leg 68 of retraction assembly 16'. In turn, retraction assembly 16' is moved downwardly such that locking port 64 engages the needle sleeve 24 in an active position as described above for the first embodiment of the invention. Thereafter, pull tabs 76 are utilized to move retraction assembly 16' rearward along the axis of barrel 14'. As described above, locking port 64 engages the flared proximal end 28 of needle sleeve 24 such that as the needle sleeve 24 is moved rearward, the needle cannula 30 is retracted rearward through the hub 18 and into the cylindrical interior of the barrel 14'. Once stop tabs 74 contact ridge 78, the movement thereof is halted and the used needle cannula 30 is safely contained within barrel 14', as shown in FIG. 15. Additionally, if desired, the legs 68, 70 of retraction assembly 16' may be bent as shown in FIG. 16 to further insure the non-movement of the used needle cannula once it has been withdrawn. As in the first embodiment above, the barrel and needle may then be safely disposed of without risk of injury. In addition, once needle 30 is retracted into barrel 14', there is no mechanism for extending needle cannula 30 and needle sleeve 24 through hub 18. Therefore, the operator is assured that needle cannula 30 will not be reused.

A further embodiment of the phlebotomy system of the present invention, is generally designated by reference numeral 100 and is illustrated in FIGS. 17–20. System 100 includes barrel 114 virtually identical to that of the above-described systems, a needle assembly 112 and a retraction assembly 116. Needle assembly 112 includes a hub 118 having a hollow core 122 extending axially therethrough and a threaded proximal end 120, a needle sleeve 124 having a hollow core 126 extending axially therethrough, a double ended needle or needle cannula 130, and a rubber sleeve or flow inhibitor 132, as shown in FIGS. 17 and 18. Needle sleeve 124 in accordance with this embodiment of the invention also includes a threaded portion 129 preferably disposed forward of the proximal end, which may be a flared proximal end 128. The hollow core 122 of hub 118 has an inner diameter approximately equal to the outer diameter of needle sleeve 124 such that the sleeve 124 may be inserted into the hollow core 122 of hub 118 in the assembled state. Similarly, the hollow core 126 of needle sleeve 124 has an inner diameter approximately equal to the outer diameter of needle cannula 130 such that needle cannula 130 may be securely positioned in the sleeve 124 within hub 118. As illustrated, a first end 134 of needle cannula 130 extends through the distal end of the sleeve and hub for insertion into a vein and the second end 136 extends through the flared proximal end 128 for attachment to an evacuated receptacle. The rubber flow inhibitor 132 is installed over the second end 136 of needle 130 and then stretched to fit over the flared proximal end 128 of the needle sleeve 124. In addition, a protective cover (not shown) may be installed over the first end 134 of the needle until such time as when an operator or technician is ready to draw blood.

Figure 19:
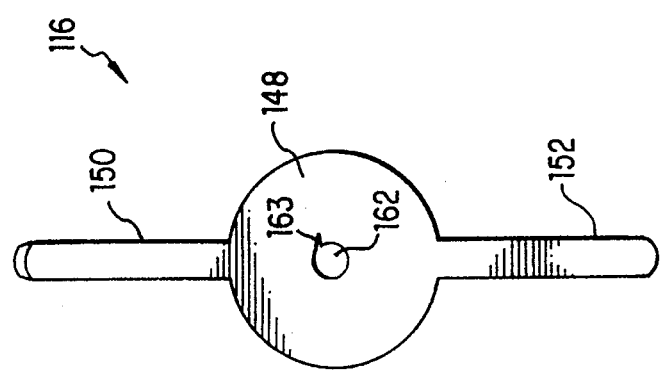
FIG. 19 is a front view of a retraction assembly of the phlebotomy system in accordance with the third embodiment of the present invention.

Retraction assembly 116 in accordance with this third embodiment of the present invention is shown in FIG. 19 and is illustrated positioned within barrel 114 in FIG. 20. Retraction assembly 116 includes a central plate 148, an upper extension 150 extending upward therefrom and a lower extension 152 extending downward therefrom. The upper extension 150 and lower extension 152 both have a finger grip 156 in order to assist the operator or technician in the proper use and positioning of the present invention. Central plate 148 includes a central opening or access port 162 extending therethrough and generally corresponding in size and shape to needle sleeve 124. Central opening 162 includes a diagonal slit 163 extending outward which allows a slight bending of central opening to form a starting edge to engage the threaded portion 129 of the needle sleeve. Therefore, a thumb tab for application of a downward force for movement to the active position is not required in this embodiment of the invention because of the fixed threaded engagement between the central plate and the needle sleeve. Similarly, the position indents and position stop of the first embodiment may be omitted because the vertical position of retraction assembly 116 is fixed by the threaded engagement between the central plate and the needle sleeve.

The above components of phlebotomy system 100 of the present invention are assembled for use in the following arrangement. The upper extension 150 of retraction assembly 116 extends through a first of the slide openings 140 of barrel 114 and the lower extension 152 extends through a second of the slide openings 140 of barrel 114. Retraction assembly 116 is positioned within barrel 114 at the forward end thereof and the slide stops prevent the rearward movement of the retraction assembly 116, as in the previously described embodiments. Needle sleeve 124 containing needle cannula 130 and rubber flow inhibitor 132 passes through the distal end opening 166 and central opening 162 such that the second end 136 of the needle cannula and the flared proximal end 138 of the needle sleeve 124 are positioned adjacent retraction assembly 116 within the barrel 114 on the proximal side of retraction assembly 116. The first end 134 of needle cannula 130 extends through the distal opening 166 of barrel for insertion into a vein and may be provided with a protection cover (not shown). The threaded distal end 138 of barrel 114 is connected by screw thread engagement with the threaded proximal end 120 of the hub 118. In accordance with this embodiment of the present invention, the threaded portion 129 of the needle sleeve 124 is similarly connected by screw thread engagement with the central opening 162 of the central plate 148 and thus, movement from a passive position to an active position in not necessary. This in turn secures the needle assembly 112 and the retraction assembly 116 within barrel 114 and phlebotomy system 100 is ready for use. Blood is withdrawn in a similar manner to that of the previously described embodiments of present invention.

When the blood withdrawal process in complete, the operator using the blood sampler 100 of the present invention retracts needle 130 into the cylindrical compartment of barrel 114, and thereby reduces the risk of injury or transmission of disease from a used needle. In this embodiment of the invention, the operator merely applies a force to retraction assembly 116 sufficient to move past forward the slide stops such that the retraction assembly is free to move axially rearward within the slide openings. Alternatively, the forward slide stops may be omitted entirely as the position indents may be omitted since there is no vertical movement of the assembly. In both cases, further rearward movement of the retraction assembly 116 within slide openings 140 causes a corresponding movement of the needle sleeve in the rearward direction since needle sleeve 124 is threadedly engaged through the central opening 162 of the retraction assembly. As the needle sleeve 124 is moved rearward, the needle cannula 130 is retracted rearward through the hub 118 and into the cylindrical interior of the barrel 114. Rear slide stops may be provided as in the previously described embodiments to terminate the movement of retraction assembly 116 and signal that the used needle cannula 130 is safely contained within barrel 114. The barrel and needle may then be safely disposed of without risk of injury.

In accordance with a fourth embodiment of the present invention, retraction assembly 116' can also be provided with a central opening 162' for threaded engagement with the threaded portion 129 of needle sleeve 124, as shown for phlebotomy system 100' in FIGS. 21–24. Retraction assembly 116' is configured for insertion into barrel 114'. Barrel 114' is virtually identical to that described above for the second embodiment of the invention, with the exception that no engagement lever is required to move the retraction assembly into the active position. Also similar to the second embodiment of FIGS. 11–16, retraction assembly 116' has a narrow, generally U-shaped configuration generally corresponding to that of barrel 114'. Retraction assembly 116' has an upper leg 168, a lower leg 170, and a base portion 172 extending therebetween and joining together the opposing legs. Base portion 172 includes the central plate 148' having a central opening 162' and diagonal slit 163' identical to that described above for retraction assembly 116. Each leg 168, 170 includes a pull tab 176 for gripping retraction assembly 116' and moving it axially along the length of barrel 14' and a stop tab 174 which limits the axial movement of retraction assembly 116'. Guide arms 188 may also be provided as in the second embodiment of the invention to position the retraction assembly 116' properly within barrel 114'.

As mentioned above, since central opening 162 is threadedly engaged with the threaded portion 129 of needle sleeve 124, no downward movement of the retraction assembly is required to obtain the active position. Accordingly, no engagement lever is provided on barrel 114' and it is merely a matter of moving retraction assembly 116' rearward to effect a retraction of the needle cannula. Thus, pull tabs 176 are utilized to move retraction assembly 116' rearward along the axis of barrel 114'. As described above, central opening 162' threadedly engages threaded portion 129 of needle sleeve 124 such that as the needle sleeve 124 is moved rearward, the needle cannula 130 is retracted rearward through the hub 118 and into the cylindrical interior of the barrel 114'. Once stop tabs 174 contact the ridge, the movement thereof is halted and the used needle cannula 130 is safely contained within barrel 114', as shown in FIG. 23. Additionally, if desired, the legs 168, 170 of retraction assembly 116' may be bent as shown in FIG. 24 to further insure the non-movement of the used needle cannula once it has been withdrawn. As in the first embodiment above, the barrel and needle may then be safely disposed of without risk of injury.

It will be obvious to one of ordinary skill in the art that numerous modifications may be made without departing from the true spirit and scope of the present invention, which is to be limited only by the appended claims.

I claim:

1. A phlebotomy system comprising:
    a needle assembly including a needle cannula having first and second ends, a needle sleeve for supporting said needle cannula and having a flared proximal end, and a hub into which said needle sleeve is inserted;
    a cylindrical barrel having a plurality of slide openings along a longitudinal axis of said barrel removably secured to the hub;
    a retraction assembly including an upper extension extending through a first of said slide openings, a lower extension extending through a second of said slide openings, and a central plate having a central opening through which said needle sleeve extends;
    wherein said needle cannula is positioned in a normal extended position through said hub and said retraction assembly is disposed in a passive position near a distal end of said barrel; and
    wherein said needle cannula is moved to a retracted position within said barrel when said retraction assembly is disposed in an active position and moved axially along said slide openings toward a proximal end of said barrel.

2. The phlebotomy system of claim 1 wherein said central opening through said central plate includes a larger access port and a tapered locking port, said access port being aligned with said needle sleeve when said needle is positioned in said normal extended position and said retraction assembly is disposed in said passive position.

3. The phlebotomy system of claim 2 wherein said retraction assembly further includes a means for receiving a downward force to said retraction assembly, said downward force repositioning said retraction assembly to said active position such that said locking port is axially aligned with and thereby engages said needle sleeve.

4. The phlebotomy system of claim 3 wherein said locking port engages said flared proximal end of said needle sleeve when said retraction assembly is moved axially along said slide openings toward said proximal end of said barrel.

5. The phlebotomy system of claim 4 wherein when said retraction assembly is moved axially along said slide openings toward said proximal end of said barrel, said needle sleeve and said needle cannula supported therein are moved a corresponding distance toward said proximal end of said barrel.

6. The phlebotomy system of claim 1 wherein said hub has a threaded proximal end and said barrel has a threaded distal end, said hub and said barrel being threadedly secured together.

7. The phlebotomy system of claim 1 wherein said barrel further includes at least one forward slide stop disposed in one of said slide openings such that rearward movement of said retraction assembly in said passive position is prevented.

8. The phlebotomy system of claim 7 wherein at least one of said upper and lower extensions includes at least one position indent corresponding in size and shape to said at least one forward slide stop whereby when a downward force is applied to said retraction assembly, said at least one position indent aligns with said at least one forward slide stop and rearward movement of said retraction assembly is permitted.

9. A phlebotomy system comprising:
    a needle assembly including a needle cannula having first and second ends, a needle sleeve for supporting said needle cannula and having a flared proximal end, and a hub into which said needle sleeve is inserted;
    a cylindrical barrel threadedly secured to said hub;
    a retraction assembly including a central plate having a central opening through which said needle sleeve extends;
    wherein said needle cannula is positioned in a normal extended position through said hub when said retraction assembly is disposed in a passive position; and
    wherein said needle cannula is moved to a retracted position within said cylindrical barrel when said retraction assembly is disposed in an active position and said central plate of said retraction assembly is moved toward a proximal end of said barrel.

10. The phlebotomy system of claim 9 wherein said central opening through said central plate includes a larger access port and a tapered locking port.

11. The phlebotomy system of claim 10 wherein said access port is aligned with said needle sleeve when said needle cannula is positioned in said normal extended position.

12. The phlebotomy system of claim 11 wherein said retraction assembly further includes a means for receiving a downward force applied to said retraction assembly, said downward force repositioning said retraction assembly to said active position such that said locking port is axially aligned with and thereby engages said needle sleeve.

13. The phlebotomy system of claim 12 wherein said locking port engages said flared proximal end of said needle sleeve as said central plate of said retraction assembly is moved toward said proximal end of said barrel.

14. The phlebotomy system of claim 13 wherein said retraction assembly is positioned within said barrel, said retraction assembly having a generally U-shaped configuration including an upper leg, a lower leg, and a base portion extending therebetween, said upper leg extending adjacent an interior upper surface of said barrel and said lower leg extending adjacent an interior opposing lower surface of said barrel.

15. The phlebotomy system of claim 14 wherein said upper and lower legs extend past said proximal end of said barrel and define pull means for moving said retraction assembly axially along said upper and lower interior surfaces of said barrel.

16. The phlebotomy system of claim 15 wherein said central plate is disposed along said base portion of said retraction assembly, said base portion being adjacent a distal end of said barrel when said retraction assembly is in said passive position.

17. The phlebotomy system of claim 9 wherein said barrel further includes a stop ridge extending around an interior circumference thereof and said retraction assembly further includes at least one stop tab such that rearward movement of said retraction assembly is halted when said stop tab contacts said ridge.

18. A phlebotomy system comprising:

a needle assembly including a needle cannula having first and second ends, a needle sleeve for supporting said needle cannula and having a threaded intermediate portion, and a hub into which said needle sleeve is inserted;

a cylindrical barrel threadedly secured to said hub;

a retraction assembly including a central plate having a central opening through which said needle sleeve extends, said central opening and said threaded intermediate portion of said needle sleeve being threadedly secured;

wherein said needle cannula is positioned in a normal extended position through said hub when said retraction assembly is disposed in a first position; and wherein said needle cannula is moved to a retracted position within said cylindrical barrel when said retraction assembly is disposed in a second position and said central plate of said retraction assembly is moved toward a proximal end of said barrel.

19. The phlebotomy system of claim 18 wherein said retraction assembly is positioned within said barrel, said retraction assembly having a generally U-shaped configuration including an upper leg, a lower leg, and a base portion extending therebetween, said upper leg extending adjacent an interior upper surface of said barrel and said lower leg extending adjacent an interior opposing lower surface of said barrel.

20. The phlebotomy system of claim 19 wherein said upper and lower legs extend past said proximal end of said barrel and define pull means for moving said retraction assembly axially along said upper and lower interior surfaces of said barrel.

* * * * *